US010780198B2

(12) United States Patent
Jeffries et al.

(10) Patent No.: US 10,780,198 B2
(45) Date of Patent: Sep. 22, 2020

(54) ELECTROSPINNING WITH SACRIFICIAL TEMPLATE FOR PATTERNING FIBROUS CONSTRUCTS

(71) Applicant: University of Pittsburgh—Of the Commonwealth System of Higher Education, Pittsburgh, PA (US)

(72) Inventors: Eric M. Jeffries, Pittsburgh, PA (US); Yadong Wang, Allison Park, PA (US); James H. Clampffer, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 625 days.

(21) Appl. No.: 15/123,581

(22) PCT Filed: Mar. 6, 2015

(86) PCT No.: PCT/US2015/019146
§ 371 (c)(1),
(2) Date: Sep. 2, 2016

(87) PCT Pub. No.: WO2015/134853
PCT Pub. Date: Sep. 11, 2015

(65) Prior Publication Data
US 2017/0072105 A1 Mar. 16, 2017

Related U.S. Application Data

(60) Provisional application No. 61/948,906, filed on Mar. 6, 2014.

(51) Int. Cl.
*A61F 2/06* (2013.01)
*A61L 27/50* (2006.01)
(Continued)

(52) U.S. Cl.
CPC .............. *A61L 27/507* (2013.01); *A61F 2/06* (2013.01); *A61F 2/07* (2013.01); *A61L 27/18* (2013.01);
(Continued)

(58) Field of Classification Search
CPC ......... A61F 2/04–2002/077; A61F 2210/0004; A61F 2210/0076; A61F 2250/0067–0068; A61F 2240/005
See application file for complete search history.

(56) References Cited

U.S. PATENT DOCUMENTS

| | | | | |
|---|---|---|---|---|
| 8,354,052 B1 | 1/2013 | Guenther et al. | | |
| 2012/0141656 A1* | 6/2012 | Orr | B05B 5/08 | 427/2.25 |

(Continued)

FOREIGN PATENT DOCUMENTS

| | | |
|---|---|---|
| WO | WO 2009/093023 | 7/2009 |
| WO | WO 2011/149836 | 12/2011 |

OTHER PUBLICATIONS

Baker et al., "The potential to improve cell infiltration in composite fiber-aligned electrospun scaffolds by the selective removal of sacrificial fibers," *Biomaterials,* vol. 29, No. 15, pp. 2348-2358, 2008 (NIH public access version, 19 pages).

(Continued)

*Primary Examiner* — Rebecca S Preston
(74) *Attorney, Agent, or Firm* — Klarquist Sparkman, LLP

(57) ABSTRACT

Methods are disclosed which combine electrospinning and a sacrificial template, such as with additive manufacturing (AM), to produce fibrous microvascular scaffolds which are biodegradable, porous, and easily handled. In one example, a process for fabricating a fibrous network construct is disclosed. The method includes electrospinning a first layer
(Continued)

of fibrous material; printing a micropatterned sacrificial template; transferring the micropatterned sacrificial template onto the electrospun fibers; electrospinning a second layer of fibrous biomaterial onto the micropatterned sacrificial template thereby encapsulating the template and generating a construct with two layers; and removing the sacrificial template, producing a fibrous construct with channels or microstructures formed therein. Also disclosed are fibrous constructs and scaffolds produced by the provided methods.

22 Claims, 9 Drawing Sheets

(51) Int. Cl.

| | |
|---|---|
| ***A61L 27/54*** | (2006.01) |
| ***D01D 5/00*** | (2006.01) |
| ***B33Y 10/00*** | (2015.01) |
| ***A61L 27/38*** | (2006.01) |
| ***A61L 27/36*** | (2006.01) |
| ***A61F 2/07*** | (2013.01) |
| ***B33Y 70/00*** | (2020.01) |
| ***B33Y 80/00*** | (2015.01) |
| ***A61L 27/18*** | (2006.01) |
| ***A61L 33/06*** | (2006.01) |
| ***D01F 6/62*** | (2006.01) |
| ***D01F 6/74*** | (2006.01) |

(52) U.S. Cl.

CPC ....... *A61L 27/3679* (2013.01); *A61L 27/3808* (2013.01); *A61L 27/3886* (2013.01); *A61L 27/50* (2013.01); *A61L 27/54* (2013.01); *A61L 33/068* (2013.01); *B33Y 10/00* (2014.12); *B33Y 70/00* (2014.12); *B33Y 80/00* (2014.12); *D01D 5/0007* (2013.01); *D01F 6/62* (2013.01); *D01F 6/74* (2013.01); *A61F 2210/0004* (2013.01); *A61F 2210/0076* (2013.01); *A61F 2230/0026* (2013.01); *A61F 2240/001* (2013.01); *A61F 2240/004* (2013.01); *A61F 2240/005* (2013.01); *A61F 2250/0067* (2013.01); *A61L 27/3804* (2013.01); *A61L 2300/42* (2013.01); *A61L 2300/606* (2013.01); *D10B 2509/06* (2013.01)

(56) References Cited

U.S. PATENT DOCUMENTS

2012/0296353 A1* 11/2012 Wagner .................. A61F 2/064 606/153
2013/0066045 A1 3/2013 Bellan et al.

OTHER PUBLICATIONS

Bellan et al., "A 3D interconnected microchannel network formed in gelatin by sacrificial shellac microfibers," *Adv. Mater.*, vol. 24, No. 38, pp. 5187-5191, 2013 (NIH public access version, 10 pages).
Coxworth, "Hybrid 3D printer produces implantable cartridge," available on the World Wide Web at http://newatlas.com/implantable-cartilage-3d-printer/25155/, Nov. 23, 2012 (2 pages).
Dalton et al., "Electrospinning and additive manufacturing: converging technologies," *Biomaterials Science,* vol. 1, No. 2, pp. 171-185, 2013.
Jeffries et al., "Micropatterning electrospun scaffolds to create intrinsic vascular networks," *Macromolecular Bioscience,* vol. 14, pp. 1514-1520, 2014.
Jeffries et al., "Fibrous microvascular scaffolds made by combined electrospinning and additive manufacturing," Abstract, *14th Biennial Meeting of the International Society for Applied Cardiovascular Biology,* Apr. 2-5, 2014 (1 page).
Kim et al., "Hybrid process for fabricating 3D hierarchical scaffolds combining rapid prototyping and electrospinning," *Macromolecular Rapid Communications,* vol. 29, No. 19, pp. 1577-1581, 2008.
Lee et al., "Micropatterned fibrous scaffolds fabricated using electrospinning and hydrogel lithography: New platforms to create cellular micropatterns," *Sensors Actuators B: Chemical,* vol. 148, No. 2, pp. 504-510, 2010.
Ortega et al., "Fabrication of biodegradable synthetic perfusable vascular networks via a combination of electrospinning and robocasting," *Biomaterials Science,* vol. 3, No. 4, pp. 592-596, 2015.
Visser et al., "Biofabrication of multi-material shaped tissue constructs," *Biofabrication,* vol. 5, 035007, 2013 (9 pages).
Wray et al., "Slowly degradable porous silk microfabricated scaffolds for vascularized tissue formation," *Adv. Funct. Mater.*, vol. 23, No. 27, pp. 3404-3412, 2013 (NIH public access version, 16 pages).
Xu et al., "Hybrid printing of mechanically and biologically improved constructs for cartilage tissue engineering applications," *Biofabrication,* vol. 5, No. 1, 015001, 2013 (10 pages).

* cited by examiner

| | PDO | PCL[9] |
|---|---|---|
| UTS [Mpa] | 9.6 ± 2.2 | 5.1 ± 0.9 |
| Strain [%] | 230 ± 54 | 417 ± 58 |
| Mod [Mpa] | 29.7 ± 4.6 | 7.5 ± 0.7 |
| SKS [N/mm²] | 142 ± 17 | 164 ± 43 |

Fabrication Part 1: Pattern electrospun fibers with template 1. 3D print PVA templates 2. Place PVA template on sheet of electrospun PGS 3. Electrospin second layer of PGS fibers on top Fabrication Part 2: Crosslink and Purify PGS 4. Assemble inlet/outlet PGS tubes within the PGS-template construct. Place entire assembly in Teflon mold for crosslinking.

5. Crosslinking @ 120°C for 48 h

6. Purify in Ethanol/water washes

Fabrication Part 3: Embed vasculature in porous matrix

ELECTROSPINNING WITH SACRIFICIAL TEMPLATE FOR PATTERNING FIBROUS CONSTRUCTS

CROSS REFERENCE TO RELATED APPLICATION

This application is the § 371 U.S. National Stage of International Application No. PCT/US2015/019146, filed Mar. 6, 2015, which was published in English under PCT Article 21(2), which in turn claims priority to and the benefit of U.S. Provisional Application No. 61/948,906, filed Mar. 6, 2014, which is hereby incorporated by reference in its entirety.

FIELD

This disclosure relates to methods of electrospinning and in particular, to electrospinning with a sacrificial template and compositions made therefrom, such as patterned fibrous structure and particularly fibrous microvascular scaffolds.

BACKGROUND

Sufficient vascularization is essential to sustaining organ viability. Although extrinsic vascularization may suffice for thin tissues, whole organs need immediate blood supply via an intrinsic source. Artificial microvascular networks fabricated by lithography typically have thick solid layers separating "vasculature" from parenchyma, limiting diffusion. Cell/gel printing techniques have progressed, but remain mechanically weak. These limitations preclude current methods from use in vivo. Although electrospun scaffolds have been explored to mimic extracellular matrix, tight fiber packing limits cell infiltration. Thus, there is a need in the art to develop methods of electrospinning which allow fibrous constracts with sufficient vascularization to be formed.

SUMMARY

Disclosed herein are methods which combine electrospinning and a sacrificial template, such as with additive manufacturing (AM), which produce fibrous microvascular scaffolds which are biodegradable, porous, and easily handled. The inventors developed a process to produce a sacrificial template, such as by ex poly(vinyl alcohol) (PVA) using an additive manufacturing device such as fused deposition modeling (FDM), and encapsulate that template by electrospinning a polymer fiber. The sacrificial template is removed, such as by dissolving in water, producing microstructures in the electrospun construct. In some examples, this method is used to introduce vascular networks into electrospun scaffolds for tissue engineering. In some examples, this method is used to construct multi-layered scaffolds with several cell types to provide vasculature to tissue engineered organs. In some examples, platforms are disclosed for 3D printing and electrospinning together on the same device.

In one particular example, a process for fabricating a fibrous network construct is disclosed. The method includes electrospinning a first layer of fibrous material; printing a micropatterned sacrificial template; transferring the micropatterned sacrificial template onto the electrospun fibers; electrospinning a second layer of fibrous biomaterial onto the micropatterned sacrificial template thereby encapsulating the template and generating a construct with two layers; and removing the sacrificial template, producing a fibrous construct with channels or microstructures formed therein. Also disclosed are fibrous constructs and scaffolds produced by the provided methods.

The foregoing and other features and advantages of the disclosure will become more apparent from the following detailed description, which proceeds with reference to the accompanying figures.

BRIEF DESCRIPTION OF THE DRAWINGS

FIG. 1A) Cross-sectional scheme for constructing MV scaffold. i. PDO is electrospun onto aluminum collector. ii. PVA MV template is printed with fused deposition modeling (FDM). iii. PVA MV template is transferred to PDO fibers. iv. A second layer of PDO fibers is electrospun onto composite. v. Scaffold is removed from aluminum and washed in water to remove PVA. FIG. 1B) Automation of FDM process allows many templates to be quickly and uniformly produced. Supporting branches shown connecting the inlet and outlet are printed as part of the continuous path and trimmed before use. FIG. 1C) Automation of FDM allows easy scaling of MV templates. FIG. 1D) SEM micrographs of scaffold with template in place (left) and after template is dissolved (right). This scaffold is fibrous and the luminal structure remains open after PVA is removed. FIG. 1E) A single-bifurcation scaffold within the bioreactor chamber was used for in vitro feasibility testing.

FIG. 2A) SEM micrograph of electrospun. PDO shows uniform fiber around 1 μm diameter. FIG. 2B) Tensile mechanical testing of PDO shows tensile strength and suture retention similar to that of PCL. Cyclic testing shows that PDO is plastically deformed. FIG. 2C) SEM micrograph of HUVEC on electrospun PDO shows sprawled morphology. FIG. 2D) Live/Dead staining of HUVEC on PDO fibers is similar to that on tissue culture polystyrene (TCPS). FIG. 2E) Viability of HUVEC on PDO fibers shows no significant cytotoxicity compared to TCPS control.

FIG. 3A) CD31/VE-cadherin staining of microvessel after 10 days culture (top-view) (Scale: 150 μm) FIG. 3B) DAPI/vWF staining of cross-sections of inlet/outlet sections after 10 days of culture (Scale: 100 μm) FIG. 3C) Perfusion of acellular and 10-day cultured scaffolds with FITC-dextran. Channels after 10 days of culture demonstrate reduced permeability. The presence of FITC-dextran beyond the channel walls indicates that channels are not yet water-tight. Pixel intensity along horizontal line is shown in graph (FIG. 3D; Scale: 1 mm)

FIG. 5A) Cross section of frozen section showing monolayer. FIG. 5B) Top view. Scale bars indicated 200 μm. * indicated channels lumen.

FIG. 7A illustrates an exemplary 3D print PVA template. FIG. 7B PVA template placed on a sheet of electrospun PGS. FIG. 7C illustrates electrospun second layer of PGS fibers on to top of PVA template.

FIG. 8A is a digital image illustrating assembled inlet/outlet PGS tubes within the PGS-template construct and placement of an entire assembly in a TEFLON mold for crosslinking. FIG. 8B is a digital image illustrating crosslinking of PGS at 120° C. for 48 hours followed by purifying PGS by ethanol/water washes.

FIG. 9A provides a series of digital images illustrating a microvascular scaffold embedded in cast collagen/GAG matrix. FIG. 9B provides a set of digital images showing PGS prepolymer electrosprayed to top and bottom of microvascular scaffold (left image) and then salt-leached PGS sheets adhered to PGS prepolymer and secured by heat crosslinking (right image).

DETAILED DESCRIPTION OF SEVERAL EMBODIMENTS

I. Overview of Several Embodiments

Figures 1A, 1B, 1C, 1D, 1E:
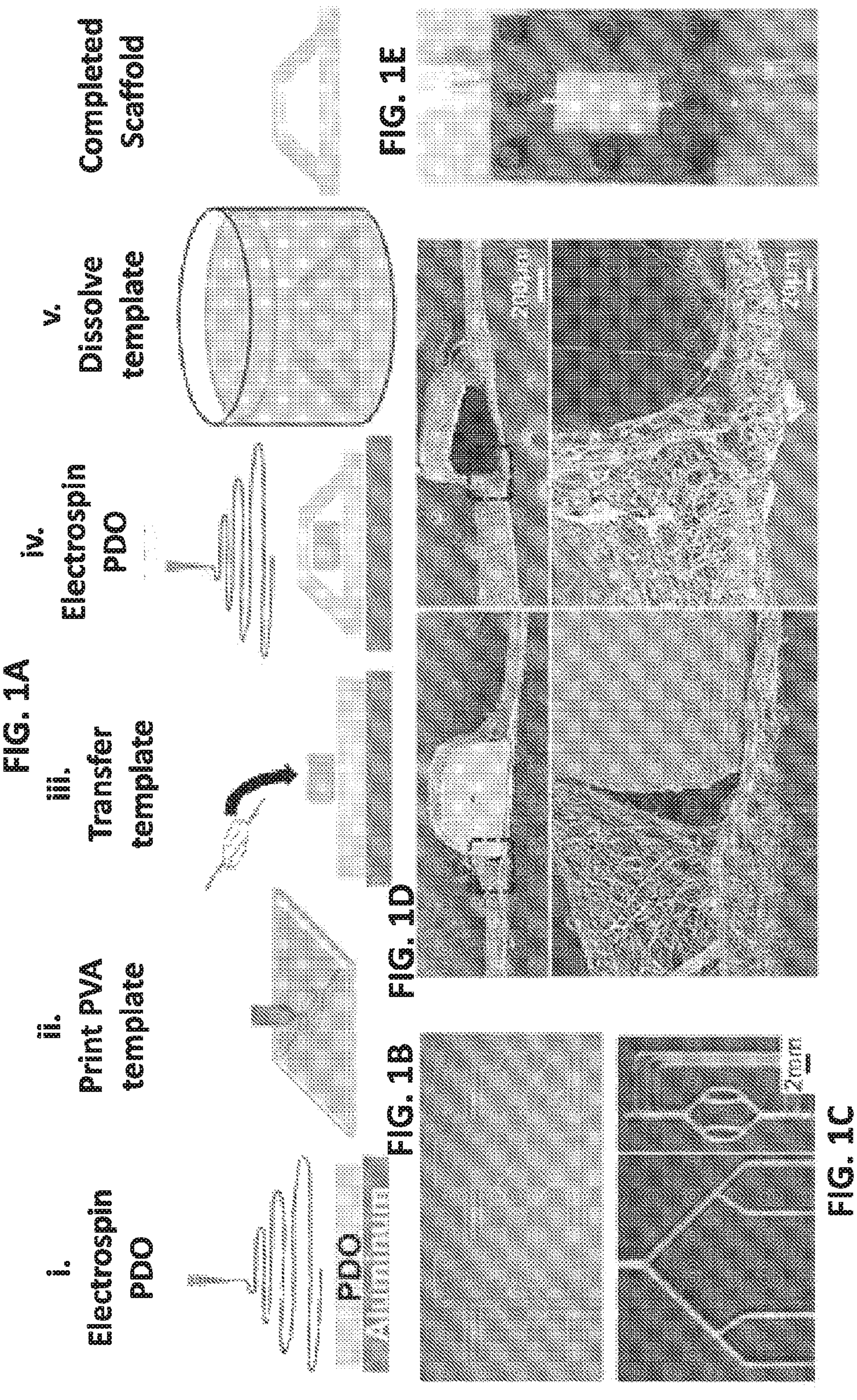
FIGS. 1A-1E. Fabrication of microvascular (MV) scaffolds by electrospinning-AM.

Disclosed herein are methods for fabricating a fibrous network construct, comprising: electrospinning a first layer of fibrous material; printing a micropatterned sacrificial template; transferring the micropatterned sacrificial template onto the electrospun fibers; electrospinning a second layer of fibrous biomaterial onto the micropatterned sacrificial template thereby encapsulating the template and generating a construct with two layers; and removing the sacrificial template, producing a fibrous network construct with channels or microstructures formed therein. The sacrificial template will be made of a polymer having an orthogonal solubility (or significantly different solubility) from the electrospun polymeric fibers.

In some embodiments, the first layer of fibrous material is a polymer, such as polydioxanone (PDO), poly(glycerol sebacale) (PGS), PGS prepolymer, poly(caprolactone) (PCL), polyethylene terephthalate (PET), polyhydroxybuytrate (PHB), poly(lactic-co-glycolic acid) (PLGA), poly (styrene-block-isobutylene-block-styrene) (SIBS), collagen, gelatin, or a combination thereof.

In some embodiments, the second layer of fibrous material is a polymer, such as PDO, PGS, PGS prepolymer, PCL, PET, PHB, PLCA, gelatin, or a combination thereof.

In some embodiments, the first layer of fibrous material and the second layer of fibrous material art the same fibrous material.

In some embodiments, the fibrous material is PDO.

In some embodiments, the fibrous material is PGS or PGS prepolymer.

In some embodiments, the first layer of fibrous material and the second layer of fibrous material are different fibrous material.

In some embodiments, electrospinning a first layer of fibrous material comprises electrospinning a first layer of fibrous material onto an aluminum collector.

In some embodiments, the micropatterned sacrificial template is formed of a water-soluble substance, such as polyvinyl alcohol (PVA), carboxymethyl cellulose, gelatin, mono- or polysaccharide PEO or PEG, or a combination thereof.

In some embodiments, printing a micropatterned sacrificial template is by one of the additive manufacturing techniques, such as by fused deposition modeling (FDM). But the template can also be fabricated using lithography based techniques.

In some embodiments, removing the sacrificial template comprises dissolving the sacrificial template in water.

In some embodiments, the sacrificial template may be a reverse thermal gel, removed by temperature change in conjunction with washing in water.

Also disclosed are fibrous constructs, scaffolds and vascular grafts formed by the provided methods.

II. Terms

Unless otherwise noted, technical terms are used according to conventional usage. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "comprises" means "includes." The abbreviation, "e.g." is derived from the Latin *exempli gratia,* and is used herein to indicate a non-limiting example. Thus, the abbreviation "e.g." is synonymous with the term "for example." Although methods and materials similar or equivalent to those described herein can be used in the practice or testing of this disclosure, suitable methods and materials are described below. In addition, the materials, methods, and examples are illustrative only and not intended to be limiting.

In order to facilitate review of the various embodiments of this disclosure, the following explanations of specific terms are provided:

Anticoagulant: A substance that prevents the clotting of blood (coagulation). Anticoagulants are commonly administered to subjects to prevent or treat thrombosis. Generally, anticoagulants are administered to treat or prevent deep vein thrombosis, pulmonary embolism, myocardial infarction, stroke, and mechanical prosthetic heart valves. Various types of anticoagulants with different mechanisms of action are available including anticoagulants that inhibit the effect of vitamin K (such as coumadin) or thrombin directly (such as argatroban, lepirudin, bivalirudin, and ximelagatran) or that activate antithrombin II that in turn blocks thrombin from clotting blood (such as heparin and derivative substances thereof).

Biocompatible: A term describing something that can be substantially non-toxic in the in vivo environment of its intended use, and is not substantially rejected by the patient's physiological system (e.g., is nonantigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of subjects, will not cause a significantly adverse reaction or response. Furthermore, biocompatibility can be affected by other contaminants such as prions, surfactants, oligonucleotides, and other agents or contaminants. The term "biocompatible material" refers to a material that does not cause toxic or injurious effects on a tissue, organ, or graft.

Biodegradable polymer: A polymer that can be cleaved either enzymatically or hydrolytically to break it down sufficiently so as to allow the body to absorb or clear it away. A biodegradable vascular graft is a graft in which at least a significant portion (such as at least 50%) of the graft degrades within one year of implantation.

Cell-free graft: A graft which does not contain cells, such as, endothelial or smooth muscle cells at the time of implantation.

Coat: As used herein "coating", "coatings", "coated" and "coat" are forms of the same term defining material and process for making a material where a first substance or substrate surface is at least partially covered or associated with a second substance. Both the first and second substance are not required to be different. Further, when a surface is "coated" as used herein, the coating may be effectuated by any chemical or mechanical bond or force, including linking agents. The "coating" need not be complete or cover the entire surface of the first substance to be "coated". The "coating" may be complete as well (e.g., approximately covering the entire first substance). There can be multiple coatings and multiple substances within each coating. The coating may vary in thickness or the coating thickness may be substantially uniform. Coatings contemplated in accordance with the present disclosure include, but not limited to medicated coatings, drug-eluting coatings, drugs or other compounds, pharmaceutically acceptable carriers and combinations thereof, or any other organic, inorganic or organic/inorganic hybrid materials. In an example, the coating is a thromboresistant coating which has anticoagulant properties, such as heparin.

Cross-link or chemical cross-linker: A cross-link is a bond, such as a covalent or ionic bond, that links one polymer chain to another. "Polymer chains" can refer to synthetic polymers or natural polymers (such as proteins). Mixing of an unpolymerized or partially polymerized resin with specific chemicals called crosslinking reagents results in a chemical reaction that forms cross-links. The resulting modification of mechanical properties depends strongly on the cross-link density. Low cross-link densities decrease the viscosities of polymer melts. Intermediate cross-link densities transform gummy polymers into materials that have elastomeric properties and potentially high strengths. Very high cross-link densities can cause materials to become very rigid or glassy, such as phenol-formaldehyde materials. In one example, a chemical cross-linker is lysine triisocyanate.

Electroaerosoling: A process in which droplets are formed from a solution or melt by streaming an electrically charged polymer solution or melt through an orifice.

Eletroproeessing: A process which includes any means of using an electrical field for depositing a material on a target.

Electrospinning: A process in which fibers are formed from a solution or melt by streaming an electrically charged solution or melt through an orifice.

Gelatin: A rapidly-degrading biocompatible material derived from collagen. Gelatin acts as a carrier for PGS to permit fiber formation by increasing fiber entanglement. Additionally, increased gelatin improves the morphology of fibers by reducing fiber fusion during electrospinning, and heat curing. Gelatin may also have benefits for promoting cell adhesion and does not need to be removed like other carrier polymers. The disclosed methods herein utilize gelatin as a natural carrier polymer.

Heat-resistant carrier polymer: A polymer with sufficiently high glass transition temperatures and/or melting temperatures such that they remain solid or semi-solid at temperatures of 100 to 150° C. such as PVA, PHB, PET, polydioxanone (PDO), or poly(lactic acid) (PLA).

Pre-polymer: A monomer or system of monomers that have been reacted to an intermediate molecular weight state. This material is capable of further polymerization by reactive groups to a fully cured high molecular weight state. As such, mixtures of reactive polymers with un-reacted monomers may also be referred to as pre-polymers. The term "pre-polymer" and "polymer precursor" may be interchanged. In some examples, a pre-PGS polymer is used in the disclosed methods to construct the disclosed PGS fibers.

Poly(caprolactone)(PCL): A biodegradable polyester with a low melting point uf around 60° C. and a glass transition temperature of about −60° C. PCL is prepared by ring opening polymerization of ε-caprolactone using a catalyst such as stannous octoate. PCL is degraded by hydrolysis of its ester linkages in physiological conditions (such as in the human body) and can be used as an implantable biomaterial.

Polydioxanone (PDO): A colorless, crystalline, biodegradable synthetic polymer. Chemically, polydioxanone is a polymer of multiple repeating ether-ester units. It is obtained by ring-opening polymerization of the monomer p-dioxanone. The process requires heat and an organometallic catalyst like zirconium acetylacetone or zinc L-lactate. It is characterized by a glass transition temperature in the range of −10 and 0° C. and a crystallinity of about 55%. For the production of sutures, polydioxanone is generally extruded into fibers. The ether oxygen group in the backbone of the polymer chain is responsible for its flexibility.

Polyethylene tereptithalate (PET): A thermoplastic polymer resin of the polyester family used in synthetic fibers. PET is formed with polymerized units of the monomer ethylene terephthalate, with repeating $C_{10}H_8O_4$ units. Clinical grade PET is an FDA approved material for vascular grafts. In some examples, PET is used as a carrier polymer in the disclosed methods and is blended with PCS.

Poly(glycerol sebacate) (PGS): An elastomeric biodegradable polyester. In some examples, PGS is electrospun with gelatin to form fibrous constructs. In some examples, PGS prepolymer is blended with a synthetic polymer such as polyvinyl alcohol (PVA), polyhydroxybuytrate (PHB) or polyethylene terephthalate (PET). In some examples, PGS prepolymer is blended with poly(lactic-co-glycolic acid) (PLGA) and a chemical cross-linker, then electrospun as a blended material. The PLGA is removed with organic solvent to leave only PGS fibers. In some examples, PGS prepolymer is blended with gelatin. In some examples, PGS is electrospun, a sacrificial template is placed on a sheet of electrospun PGS and a second layer of PGS fibers are electrospun on top of the sacrificial template.

Polyhtydroxybuytrate (PHB): A polyhydroxyyalkanoate (PHA), a polymer belonging to the polyesters class that is of interest as bio-derived and biodegradable plastics. PHB has a melting point 175° C., glass transition temperature 2° C. and a tensile strength 40 MPa, close to that of polypropylene. In some examples, PHB is used as a carrier polymer in the disclosed methods and is blended with PGS prepolymer prior to electrospinning and crosslinking.

Polyvinyl alcohol (PVA): PVA is a synthetic polymer produced by partial or full hydrolysis of polyvinyl acetate with solubility and crystallinity dependent on the degree hydrolysis and polymerization. PVA is nontoxic, noncarcinogenic, and approved for food contact by FDA. PVA hydrogels have been implanted for a variety of applications including tissue adhesion barriers, nerve guides, and cartilage replacement. PVA is water soluble and retains GRAS (generally recognized as safe) status with the FDA as a food additive. In some examples, PVA is used to form the patterned template.

Scaffold: A structural support facilitating cell infiltration and attachment in order to guide vessel growth. As disclosed herein, a biodegradable scaffold can be used to form a vascular graft. In some examples, a biodegradable scaffold includes electrospun PGS or electrospun PDO.

Subject: Living multi-cellular vertebrate organisms, a category that includes human and non-human mammals (such as laboratory or veterinary subjects). In an example, a subject is a human. In an additional example, a subject is selected that is in need of an implant for damaged or defective artery.

Vascular graft: A tubular member which acts as an artificial vessel. A vascular graft can include a single material, a blend of materials, a weave, a laminate or a composite of two or more materials.

III. Methods of Fabrication and Compositions therefrom

Current microfluidic platforms are not suitable for in vivo environments. Described herein are methods for patterning microvascular structures in fibrous electrospun scaffolds with soluble, sacrificial templates, such as by additive manufacturing (AM). The fibrous structure mimics extracellular matrix (ECM) and permits diffusion and cell infiltration. It is contemplated that any polymer which can be electrospun may he used in the disclosed method to form the fibrous electrospun scaffolds. The generated fibrous scaffolds are biodegradable and suturable. In contrast to previous methods that describe electrospun fibers as the template, the electrospun fibers herein make-up the bulk of the scaffold. The disclosed methods allow customized scaffolds to be formed by using customized and intricate template designs in the manufacturing process.

In some embodiments, a method of fabricating a fibrous construct comprise electrospinning a fibrous biomaterial, such as a polymer, including, but not limited to PDO, PCL, PGS, PET, PHB, PLGA, gelatin, PGS pre-polymer or any combination. In some examples, the polymer is electrospun onto an aluminum collector. The method also comprises printing (such as by additive manufacturing) a sacrificial template, such as a micropatterned sacrificial template formed of PVA. Acetonitrile butyl styrene (ABS) or (PLGA) are commercially-available as FDM filaments and may be used as templating materials. However, these would require an organic solvent for removal. It is contemplated that other thermoplastic materials (e.g., PCL) known to those of one of ordinary skill in the art can be used for printing templates. These are not currently available in filament form and would require additional processing or modification of the extruder. Hydrogels can also be used as templates if the FDM extruder is replaced by a syringe. The sacrificial template is then transferred/placed onto the electrospun fibers. A second layer of fibrous biomaterial, such as a polymer (e.g., PDO, PGS, PET, PHB, PLGA, gelatin, PGS pre-polymer or any combination) is electrospun onto the sacrificial template thereby encapsulating the template and generating a construct with two layers. The number of layers may vary depending upon the desired pattern or use of the scaffold. It is also contemplated that the polymers may vary amongst the different layers. The sacrificial template is removed, such as by dissolving the template in water, producing a fibrous construct with channels or microstructures formed therein. In some examples, the sacrificial template is patterned to allow at least one interconnected channel pattern form within the matrix and wherein at least one interconnected channel pattern has diameters ranging from 0.01 mm to about 1 mm, such as between 0.1 mm and 0.8 mm, between 0.3 mm and 0.7 mm, between 0.2 and 0.5 mm, between 0.05 mm and 0.5 mm, between 0.01 mm and 0.1 mm, including 0.01, 0.02, 0.03, 0.04, 0.05, 0.06, 0.07, 0.08, 0.09, 0.1, 0.2, 0.3, 0.4, 0.5, 0.6, 0.7, 0.8, 0.9 or 1 mm.

In one embodiment, the method comprises electrospinning PDO onto an aluminum collector; printing a micropatterned sacrificial template formed of PVA by additive manufacturing using FDM; transferring the PVA template onto the electrospun PDO fibers; electrospinning a second layer of PDO onto the sacrificial template thereby encapsulating the template and generating a scaffold with two layers; and dissolving the template by exposure to water, thereby producing a fibrous construct with channels or microstructures formed therein. This exemplary method is illustrated in FIG. 1A.

Figure 6:
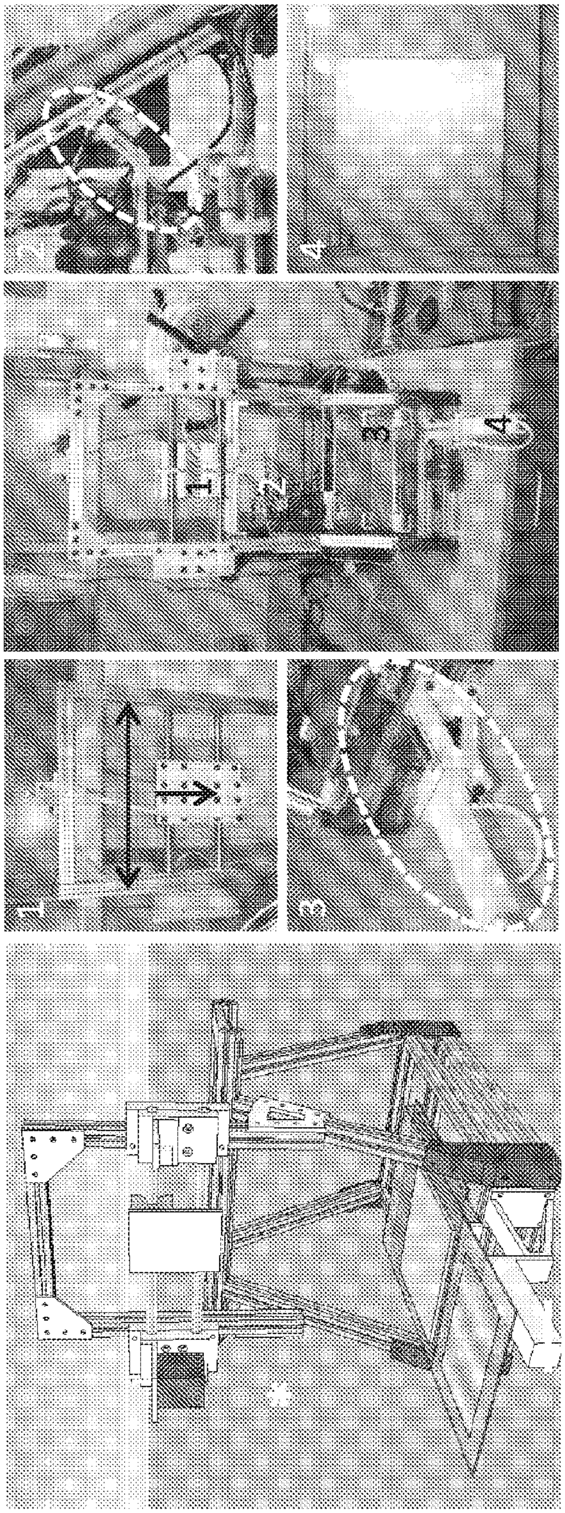
FIG. 6 illustrates the combining electrospinning with 3D printing on the same platform.

In some examples, the method comprises combining electrospinning with 3-dimensional printing on the same platform. An example of this is shown in FIG. 6. The electrospinning and FDM templating can be performed on the same platform using a modified FDM as shown in FIG. 6. This eliminates the need to transfer the template from the print platform to the electrospun sheet. This is ideal for creating multi-layered structures since this allows automation of the two processes increasing in the z-dimension (height). The limitation of this process is that the template material may melt the electrospun material depending on melting points of each material.

FIG. 6 (left) shows computer-rendered model of a Lulzbot FDM printer that has been modified for electrospinning capabilities. FIG. 6 (right) is a photograph of the Lulzbot FDM modified for electrospinning. (1) A syringe-holder is attached to a gantry above the platform. Electrospun fibers are ejected from this point as performed normally during electrospinning. The syringe holder is motorized to allow motion of the electrospinning syringe and better coverage of the collector plate. (2) A solvent dropper that can be advanced/retracted by solenoid is attached to the extruder platform. This may be used to selectively remove points of electrospun layers for multi-layer fabrication. (3) A spring-activated contact is attached to provide a negative charge to the collector when electrospinning. The collector disengages from negative charge when extruding. This protects the extruder electronics front high voltage of electrospinning. (4) A modified collector plate replaces the standard printing platform. This plate contains aluminum that is isolated from underlying platform by insulating acrylic. A conducting contact is bored through the acrylic to engage with the negatively-charged spring (3). All metal points of the platform are connected and grounded to reduce charge accumulation and risk of electronic damage from high voltage shock.

Figure 8A:
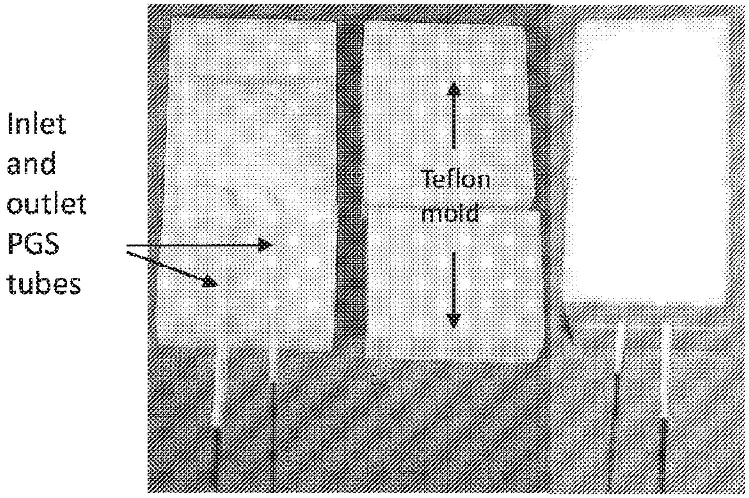
FIGS. 8A and 8B illustrate an exemplary fabrication process part 2: cross link and purify PGS.
Figure 8B:
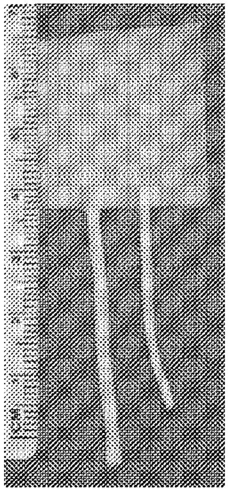
Figure 9A:
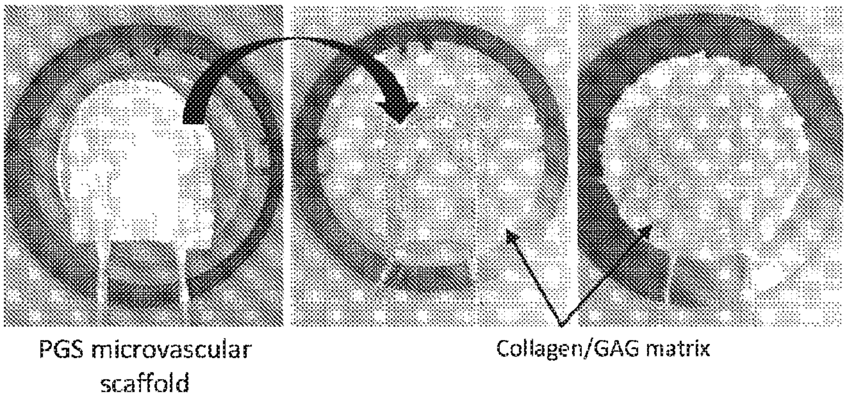
FIGS. 9A and 9B illustrate an exemplary fabrication process part 3: embed vasculature in a porous matrix.
Figure 9B:
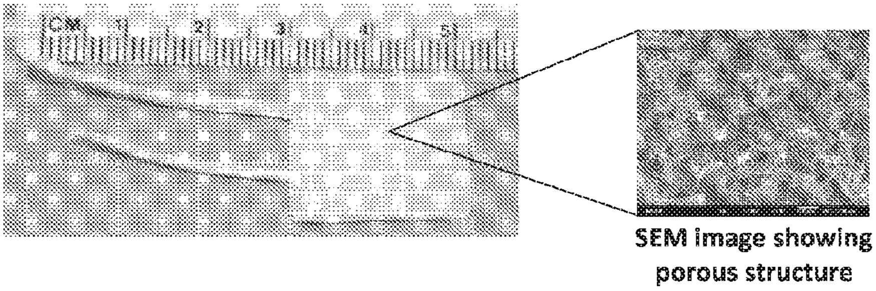
Figure 10A:
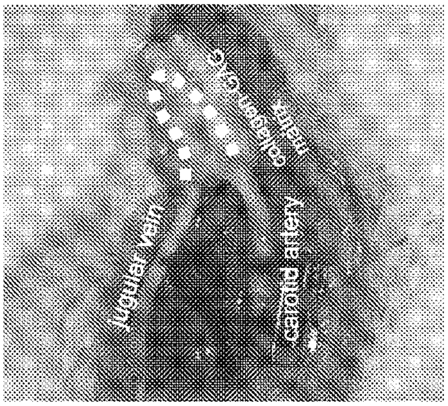
FIGS. 10A-10C provide a series of digital images of an AV shunt implant.
Figure 10B:
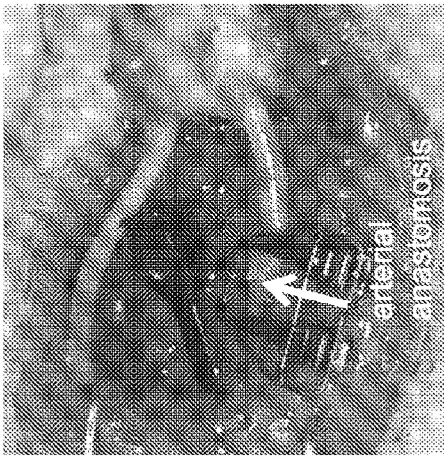
Figure 10C:

In some examples, a PGS microvascular scaffold is fabricated by the following three step fabrication process: (1) pattern electrospun fibers with template (see FIGS. 7A-7C); (2) crosslink and purify PGS constructs (see FIGS. 8A-8B); and (3) embed vasculature in a porous matrix (see FIGS. 9A-9B). For example, a 3D print PVA template is placed on a sheet of electrospun PGS and a second layer PGS is then electrospun on top of the PVA template to encapsulate the template and generate a scaffold with multiple layers. Then, the resulting construct is crosslinked, such as by assembling inlet/outlet PGS tubes within the PGS-template construct and placing the entire assembly into a TEFLON (trademark of DuPont) mold (FIG. 8A) and applying heat for a period of time sufficient for effective crosslinking (such as at 120° C. for 48 hours). Tubular inlet/outlet ports were fabricated as previously described in PCT/US2013/077226 which is hereby incorporated by reference in its entirety. TEFLON molds may be used to prevent warping/curling of the PVA templates during crosslinking. Also, the molds apply moderate pressure to select locations to facilitate better adhesion between layers of electrospun PGS layers. Pressure may be increased as necessary as a means to increase binding between the layers. In some examples, the inlet and outlet PGS tubes are placed on the same side of the construct as for some tissues it is beneficial to have the arterial and venous anastomosis sites on the same side. Further, in some examples, the PGS inlet/outlet tubes are fabricated by rotational electrospinning. Other configurations are contemplated such as the tubes being placed on opposite sides or anywhere in between. After crosslinking, the PGS is purified by ethanol/water washes. The resulting PGS microvascular scaffold can then be embedded into a porous matrix such as a cast collagen/glycosaminoglycans(GAG) matrix (FIG. 9A) or a PGS prepolymer may be electrosprayed to the top and bottom of the microvascular scaffold, salt-leached PGS sheets being adhered to PGS sheets to PGS prepolymer and secured by heat crosslinking (FIG. 9B).

The disclosed methods can be utilized to form highly porous matrices which create 3-dimensional scaffolds for cell ingrowth from the host or cell seeding for tissue engineered organ approaches. In some examples, the disclosed method is utilized to generate a vascular graft with a shaped based upon the shape of the structure, such as a blood vessel, the resulting vascular graft is replacing. In some examples, a PGS or PDO tube is formed. The generated grafts are suturable.

In some examples, the fabricated scaffold or graft comprises pores of about 1 μm to about 500 μm, from about 10 μm to about 300 μm, about 20 μm to about 300 μm, about 1 μm to about 10 μm, about 3 μm to about 7 μm, such as 1 μm, 2 μm, 3 μm, 4 μm, 5 μm, 6 μm, 7 μm, 8 μm, 9 μm, 10 μm, 11 μm, 12 μm, 13 m, 14 μm, 15 μm, 16 μm, 17 μm, 18 μm, 19 μm, 20 μm, 30 μm, 40 μm, 50 μm, 60 μm, 70 μm, 80 μm, 90 μm, 100 μm, 150 μm, 200 μm, 250 μm, 300 μm, 350 μm, 400 μm, 450 μm, or 500 μm. In some examples, pores are about 20 μm to about 30 μm, including about 20 μm, 21 μm, 22 μm, 23 μm, 24 μm, 25 μm, 26 μm, 27 μm, 28 μm, 29 μm, and 30 μm. In some examples, the scaffold or graft is fabricated to include uniformly distributed pores. In some examples, the scaffold or graft is fabricated to include non-uniformly distributed pores. In some examples, the scaffold or graft is fabricated to not include any pores.

In some examples, the scaffold or graft is fabricated to include at least 75% pore interconnectivity, such as about 80% to about 90%, about 90% to about 98%, including 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% interconnectivity.

The various dimensions of a disclosed scaffold or vascular graft may vary according to the desired use. In some examples, the method of fabrication is performed to generate a vascular graft with an inner diameter which matches that of the host vessel to be replaced. In some examples, the inner diameter is between about 1 mm to 5 mm. In some examples, a disclosed vascular graft has an inner diameter of between about 700 μm to about 5000 μm, such as about 710 μm to about 4000 μm, such as about 720 μm to about 3000 μm, such as about 1000 μm to about 5000 μm, including 710 μm, 711 μm, 712 μm, 713 μm, 714 μm, 715 μm, 716 μm, 717 μm, 718 μm, 719 μm, 720 μm, 721 μm, 722 μm, 723 μm, 724 μm, 725 μm, 726 μm, 727 μm, 728 μm, 729 μm, 730 μm, 731 μm, 732 μm, 733 μm, 734 μm, 735 μm, 736 μm, 737 μm, 738 μm, 739 μm, 740 μm, 741 μm, 742 μm, 743 μm, 744 μm, 745 μm, 746 μm, 747 μm, 748 μm, 749 μm, 750 μm, 800 μm, 850 μm, 900 μm, 950 μm, 1000 μm, 2000 μm, 3000 m, 4000 μm or 5000 μm. In some examples, the inner diameter of a disclosed vascular graft is fabricated to be about 720 μm. In some examples, the inner diameter of a disclosed vascular graft is fabricated to be about 1000 μm. In some examples, the inner diameter of a disclosed vascular graft is fabricated to be about 1200 μm. In some examples, the inner diameter of a disclosed vascular graft is fabricated to be about 2000 μm. In some examples, the inner diameter of a disclosed vascular graft is fabricated to be about 3000 μm.

In some examples, the method of fabrication is performed to generate a vascular graft with a wall thickness which matches that of the host vessel to be replaced. However, it is contemplated the graft wall can be fabricated with a thicker or thinner wall than that which is being replaced, if desired. In some examples, a disclosed vascular graft is fabricated to have a wall thickness between about 100 μm and about 500 μm, such as about 150 μm and about 450 μm, including about 200 μm and about 400 μm, such as about 100 μm, 125 μm, 150 μm, 175 μm, 200 μm, 225 μm, 250 μm, 275 μm, 300 μm, 325 μm, 350 μm, 375 μm, 400 μm, 425 μm, 450 μm, 475 μm, or 500 μm. In some examples, a disclosed vascular graft is fabricated to have a wall thickness between about 270 μm and about 300 μm, such as about 285 μm and about 295 μm, including 270 μm, 271 μm, 272 μm, 273 μm, 274 μm, 275 μm, 276 μm, 277 μm, 278 μm, 279 μm, 280 μm, 281 μm, 282 μm, 283 μm, 284 μm, 285 μm, 286 μm, 287 μm, 288 μm, 289 μm, 290 μm, 291 μm, 292 μm, 293 μm, 294 μm, 295 μm, 296 μm, 297 μm, 298 μm, 299 μm, or 300 μm. In some examples, the wall thickness is about 290 μm.

In some examples, the method of fabrication are performed to generate a scaffold or vascular graft that at least 50%, such as about 55% to about 70%, about 80% to about 90%, about 90% to about 98%, including 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% of such vascular graft degrades within one year, such as within 1 to 10 months, including within 1 month, 2 months, 3 months, 4 months, 5 months, 6 months, 7 months, 8 months, 9 months, 10 months, 11 months, or 12 months of implantation.

In some examples, the method of fabrication includes generating a cell-free scaffold or graft, such as a cell-free vascular graft, in which the graft does not include any living cells, such as smooth muscle cells, endothelial cells, stem cells, or progenitor cells.

In further examples, the disclosed methods of fabrication include impregnating or coating a surface of a generated fiber, scaffold or graft with a biocompatible and/or biodegradable material. It is contemplated that one of ordinary skill in the art can determine with but limited experimentation, which substrates are suitable for a particular application. In some examples, the inner luminal surface of the biodegradable scaffold is coated with a biocompatible and/or biodegradable material. It is contemplated that such coating may be complete or partial. In some examples, the outer (abluminal) surface of the biodegradable scaffold is coated with a biocompatible and/or biodegradable material. It is contemplated that such coating may be complete or partial.

In some examples, the disclosed methods of fabrication include impregnating or coating a surface of a generated fiber, scaffold or graft with one or more, such as two, three, four, five etc. suitable pharmaceutical agents. It is contemplated that suitable pharmaceutical agents can be organic or inorganic and may be in a solid, semisolid, liquid, or gas phase. Molecules may be present in combinations or mixtures with other molecules, and may be in solution, suspension, or any other form. Examples of classes of molecules that may be used include human or veterinary therapeutics, cosmetics, nutraceuticals, agriculturals such as herbicides, pesticides and fertilizers, vitamins, salts, electrolytes, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, minerals, plasticizers, ions, electrically and magnetically reactive materials, light sensitive materials, anti-oxidants, molecules that may be metabolized as a source of cellular energy, antigens, and any molecules that can cause a cellular or physiological response. Any combination of molecules can be used, as well as agonists or antagonists of these molecules.

Pharmaceutical agents include any therapeutic molecule including, without limitation, any pharmaceutical substance or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfiram and disulfiram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, hurnectants, rejection/anti-rejection drugs, spermicides, conditioners, antibacterial agents, antifungal agents, antiviral agents, antibiotics, tranquilizers, cholesterol-reducing drugs, antitussives, histamirw-blocking drugs, monoamine oxidase inhibitor. All substances listed by the U.S. Pharmacopeia are also included within the substances of the present disclosure.

In some examples, the inner luminal surface of a biodegradable scaffold is coated partially or completely with a thromboresistant agent, such as hepatin and/or other compounds known to one of skill in the art to have similar anti-coagulant properties as heparin, to prevent, inhibit or reduce clotting within the inner lumen of the vascular graft.

Methods of Use

The disclosed methods can be used to electrospin polymers to form scaffolds of any desired shape, such as sheets, tubes, meshes, pseudo 3-dimensional constructs. It is contemplated that the constructs may be of high porosity, low porosity, a combination of different porosity. In some examples, the methods are utilized to form vascularized (micro-channeled) fibrous sheets, random meshes, aligned sheets, cylindrical tubes, or pseudo 3-dimensional constructs, such as shapes to mimic organs. In some examples, complex shapes such as those mimicking organs are formed by the disclosed methods. The disclosed methods of electrospinning with a sacrificial template can be used to create highly porous scaffolds to mimic ECM. These structures are especially useful for applications in soft and elastomeric tissues. It is contemplated that the disclosed methods can be used to generate constructs/scaffolds used to guide host tissue remodeling in many different tissues, including any tissue that has progenitor cells. The biodegradable scaffold can be used to facilitate tissue regeneration in vivo by providing a structural frame for which tissue regeneration can occur. In some examples, the polymer is electrospun such that it allows and facilitates the infiltration of host cells including progenitor cells. In some examples, the composition is such that it allows and facilitates host remodeling of the polymer, so that eventually the polymeric structure is replaced by the desirable host tissue. It is contemplated that the methods of fabrication disclosed herein can be modified as desired by one of ordinary skill in the art to fabricate a graft with the appropriate dimensions and features depending upon tissue which is to be replaced.

In some particular examples, the generated tissue constructs are for the replacement and/or repair of damaged native tissues. For example, the disclosed constructs are contemplated to be implantable for tensile load bearing applications, such as being formed into tubular networks with a finite number of inlets and outlets. These structures can be either seeded with cells or implanted directly and relying on the host to serve as cell source and "bioincubator". These structures can be implanted as artificial organs and the inlets and outlets will be connected to host vasculature. Fiber morphology can be varied. For example, the degree of fiber fusion can be varied based on the ratio of the various polymers, such as the ratio of PGS pre-polymer:PLGA, PGS pre-polymer:PVA blends, PGS pre-polymer:PHB blends, PGS pre-polymer:PET blends or PGS:gelatin. Fiber fusion can be useful to render sheets watertight but still retain superior strength to casted sheets. It is contemplated that the disclosed methods can be used to generate stronger constructs, such as constructs to be directly implanted in subjects into load bearing environments without additional mechanical support. Uses range from vascularized sheets for hernia repair, prolapse, and wound dressings, to complex tubes for blood vessel, nerve and trachea repair. Additionally, aligned random transition spinning may be useful for ligament-bone interfaces.

In some examples, the vasculature itself maybe valuable without parenchymal cells. For example in treating ischemic diseases. The microvascular mimetics can be connected directly to a host vessel and quickly perfuse an ischemic ama of the body.

The following examples are provided to illustrate certain particular features and/or embodiments. These examples should not be construed to limit the disclosure to the particular features or embodiments described.

EXAMPLES

Example 1

Materials and Methods

This example provides the Materials and Methods for the studies described herein.

Printing of micropatterned template: A 3D printer (A-101, Lulzbot, Loveland, Colo.) was used to extrude two-dimensional capillary networks from 3 mm PVA filament (Ultimachine, South Pittsburg, Tenn.). Designs of the template were written in Goode by a custom script. Open source program Pronterface was used to control the printer and run the G-code. Printing was performed at 210° C. nozzle temperature and 120° C. bed temperature. The bed was covered by blue painter tape (3M ScotchBlue 2090) for adhesion to the print bed.

Hybrid electrospinning-AM: An 11% PDO (Sigma-Aldrich, St. Louis, Mo.) solution was prepared by dissolving in 1,1,3,3,3-hexafluoroisopropanol (HFIP, Oakwood Products Inc, West Columbia, S.C.). This solution was pumped through a 22 gauge needle at 29 μL/min with 7 kV (+) on the needle and 7 kV (−) on the aluminum collector, placed 20 cm away, PDO was deposited to an aluminum collector by vertically electrospinning 350 μL (FIG. I1A-i). A PVA template was printed (FIG. 1A-ii.) and placed on PDO fibers (FIG. 1A-iii). A second layer of PDO was deposited (FIG. 1A-iv). The layered scaffold was removed from the aluminum collector and washed twice in deionized water with agitation for 24 hours to remove PVA (FIG. 1A-v). Exel PTFE safelet I.V. catheters were inserted into the inlet and outlet channels and secured by PTFE sealant tape to provide connections for the bioreactor tubing (FIG. 1E).

Scanning electron microscopy (SEM): Dehydrated samples were sputter-coated with 3.5 nm gold with a sputter coater (Cressington). Images were taken at 3 kV acceleration voltage with a field emission SEM (JSM-6330F, Jeol, Tokyo, Japan).

Mechanical testing: The material properties of Evonik PDO were characterized since most published literature referenced Ethicon suture PDO. Dogbone-shaped samples of electrospun PDO sheets were punched using a custom die fashioned. The thickness of hydrated samples was measured with a Mitsutoyo caliper before performing uniaxial tensile tests to failure at 25 mm/s using a 50 N load cell on a MTS Insight (Eden Prairie, Minn.). Cyclic tensile tests (5 cycles) were also performed to measure elastic recovery after 50% strain. Suture retention strength was performed similar to methods described by Hong et al. (*Biomaterials,* 32, 3387). A 6-0 suture was inserted 2 mm from the end of square sample and pulled until rupture. Suture retention strength was calculated as load/(suture, diameter×sample thickness).

HUVEC attachment and viability on PDO fibers: HUVECs (Lonza, Walkersville, Md.) were cultured on fibronectin-coated (1 μg/cm$^2$; Chemicon International, Temecula, Calif.) plates using endothelial basal medium-2 (Lonza) supplemented with 10% fetal bovine serum (Hyclone, Logan, Utah), 1% L-glutaraine-penicillin-streptomycin (Mediatech, Manassas, Va.), and endothelial growth medium-2 SingleQuot Kit (Lonza), Fibrous PDO sheets were cut to circular samples 12 mm in diameter and placed under metal rings (inner diameter 7.5 mm 24-well plates. They were sterilized with 70% ethanol, rinsed with PBS, and incubated with culture medium at 37° C. for 24 h. HUVECs (passage 4) were seeded at 1.0×10$^6$ cells/mL and cultured for 1 day under static conditions. Viability was determined by Live/Dead assay (Invitrogen, Carlsbad, Calif.). Attachment was evaluated by morphological observations under SEM after serial dehydration by ethanol and hexamethyldisilazane.

Bioreactor Culture: For endothelialization, the fibrous PDO scaffold was transferred into a specially designed circulating perfusion setup. Briefly, the bioreactor chamber was made with polycarbonate sheets (thickness 2.4 mm) and a silicon rubber (thickness 3.1 mm). The fibrous PDO scaffold was connected by PTFE sealant tape. The lumen of the fibrous PDO scaffold was seeded with 1 ml of culture medium containing 1.0×10$^6$ trypsinized HUVECs. Cells were allowed to attach uniformly to the scaffold lumen by rotating the chamber as 2 rpm for 4 h. After rotation, the bioreactor chamber was attached to the perfusion setup and the scaffolds were perfused with fresh medium by using a peristaltic pump as a rate of 0.6 ml/min for 10 days. Medium was changed at every other day.

Immunofluorescence staining: Fibrous PDO scaffolds were harvested on day 10 and washed with PBS. Both inlet and outlet channels were cut from scaffolds, embedded in Tissue-Tek optimal cutting temperature compound (Sakura Finetek Inc., Torrance, Calif.) and snap-frozen in liquid nitrogen, 8-μm thick cryosections (for cross-sectional view) and other parts of scaffolds (for top-down view) were fixed in 4% paraformaldehyde for 10 min at room temperature and rinsed twice with PBS. Tissue sites of each slide were blocked with 5% normal goat serum (Sigma) for 1 h at 37° C., incubated with primary antibodies 1% goat serum for 45 min at 37° C., and incubated with secondary antibodies in 1% goat serum for 45 min at 37° C. For HUVEC staining, rabbit polyclonal anti-human CD31 (1:100; Santa Cruz Biotechnology, Dallas, Tex.) and von Willibrand factor (vWF) (1:200; Abeam, Cambridge, Mass.) were used as primary antibodies and Alexa Fluor 594 goat anti-mouse IgG (1:400; Invitrogen) and secondary antibody. For visualization of cell-to-cell junctions, rabbit polyclonal anti-human VE-cadherin (1:100; Santa Cruz) and Alexa Fluor 488 goat anti-rabbit IgG (1:200; Invitrogen) were used as primary and secondary antibodies. Nuclei were stained with 4',6-diamidino-2-phenylindole (DAPI; Invitrogen), Fluorescent images were viewed and captured with an inverted microscope (Eclipse Ti-E; Nikon Instruments, Melville, N.Y.).

Visuolizaiion of the microchannel by dextran perfusion: The bioreactor chamber was detached from the perfusion setup on day 10 and culture medium was aspirated from the lumen of microvascular channels of fibrous PDO scaffolds. FITC-labeled dextran (150 kDa, Sigma) solution was prepared by dissolving in PBS (20 mg/mL) and injected into the lumen to visualize perfused microvascular channels through endothelial cell harder. Fluorescent images were viewed and captured with an inverted microscope. Acellular PDO scaffolds were used as a negative control. The intensity of fluorescence in perfused microvascular channels was measured using the NIS-Elements software (Nikon).

Example 2

This example demonstrates vascular patterning within microfibrous structures-from 3D printing and electrospinning to endothelialization Sufficient vascularization is essential to sustaining organ viability. Although diffusion may suffice for thin tissues, vital organs require immediate blood supply via host vasculature. Microvasculature that can provide efficient mass transfer for 3D tissue has been the bottleneck of tissue engineering of vital organs for decades. Current microfluidic platforms such as soft lithography are not suitable for in vivo environments since they are often made from thick solid walls separating "vasculature" from parenchyma and limiting diffusion. Alternatively, hydrogels produced by printing or casting are weak and degrade rapidly. These shortcomings are recognized in recent literature. The disclosed approach to solve this challenge is to micropattern a completely fibrous structure using additive manufacturing (AM). The inventors electrospun biodegradable polymers to surround soluble microvascular templates produced by 3D printing. Porous structures greatly increase diffusion compared with solid-walled substrates and hydrogels. Electrospun fibers at the micro- to nano-scale are known to mimic the fibrous environment of extracellular matrix (ECM). Furthermore, the polydioxanone (PDO) fibers used to make these scaffolds is strong immediate perfusion of the implant.

Previously disclosed was the technique of templated electrospinning using linear templates to create channels in nerve guides. Advances in the AM process known as fused deposition modeling (FDM) allow one to automate the template production while creating more complex branched templates that are otherwise unavailable. These templates are printed with water-soluble polyvinyl alcohol (PVA), making removal simple and free of organic solvents. PVA is nontoxic, noncarcinogenic, and generally regarded as safe by USFDA. PVA has been used in tissue adhesion barriers, nerve guides, and cartilage replacement.

FDM presents both advantages and challenges as a templating strategy. FDM offers an inexpensive high-throughput route to producing complex structures. However, adhering the first layer to the print bed is typically the most difficult and is the only layer being printed in the present application to demonstrate feasibility of combining FDM and electrospinning to produce microvascular structures. Use of a continuous path and optimized printing, conditions (e.g., nozzle temperature, bed, temperature, level bed, and dry filament) were involved, in achieving reproducible results (FIG. 1B). Automating the template production allows us to create channels (500 μm diameter) while easily scaling or modifying the design (FIG. 1C). Diameters in this range are similar to small arteries and venules and will provide intrinsic (i.e. host) blood to the most of the tissue (A. C. Burton, Am J Physiol1951, 164, 319). The print platform may be adapted for more precise technology such as pressure assisted microsyringe (PAM), allowing capillary-level resolutions at 10-30 μm. The fusing process used by FDM tends to produce tetnplates with square cross-sections as observed in (FIG. 1D).

Figure 3A:
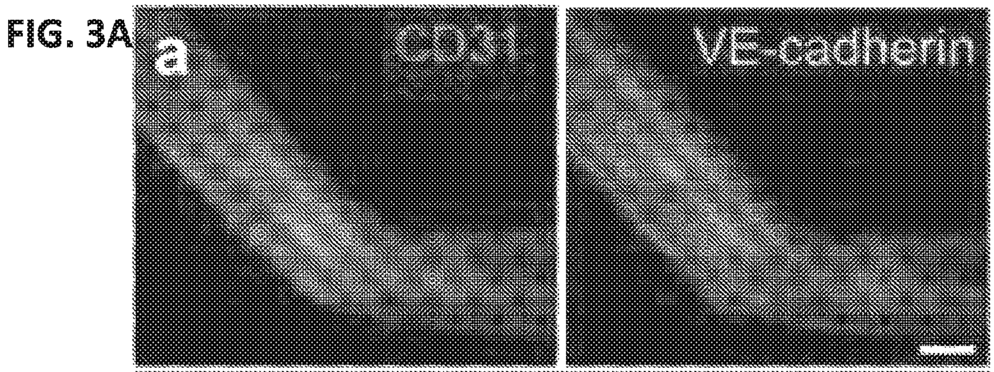
FIGS. 3A-3D illustrate in vitro endothelialization of fibrous microvascular scaffolds.
Figure 3B:
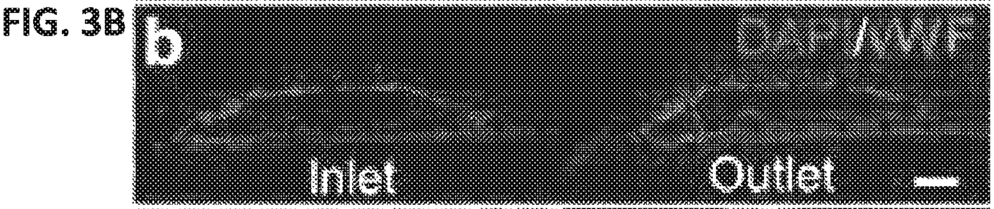

An exemplary scheme for fabricating microvascular scaffolds is provided in FIG. 1A. In this example, templates were transferred from the printing bed to the electrospinning platform because the high heat (210° C.) needed to extrude PVA melts common degradable polyesters. Electrospun PDO layers are fibrous and deposit tightly around the PVA template (FIG. 1D). As template height increases, electrospun fibers do not encapsulate the template as tightly, resulting in an isosceles trapezoidal shape (FIG. 3B). It is believed that use of elastomeric fibers will yield more circular shapes once placed under systemic blood pressure. PDO fibers retain the channel shape even after PVA is dissolved (FIG. 1D) transferring the vascular bed pattern to the fibrous scaffold. A simplified single-bifurcation scaffold was cultured in a bioreactor to test feasibility of endothelializing the fibrous microvessels (FIG. 1E).

Figure 2A:
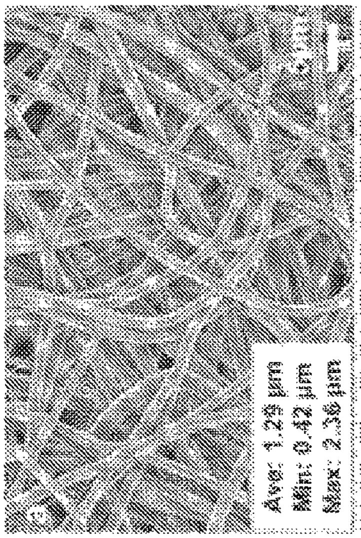
FIGS. 2A-2E illustrate the characterization of PDO microfibers for MV scaffold.
Figure 2B:
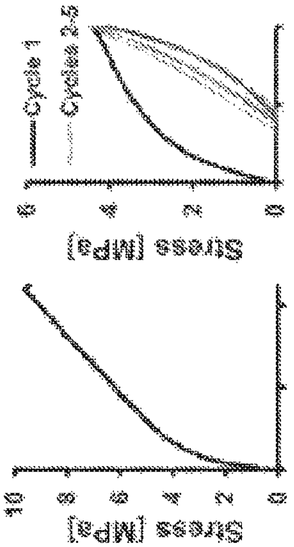
Figure 2C:
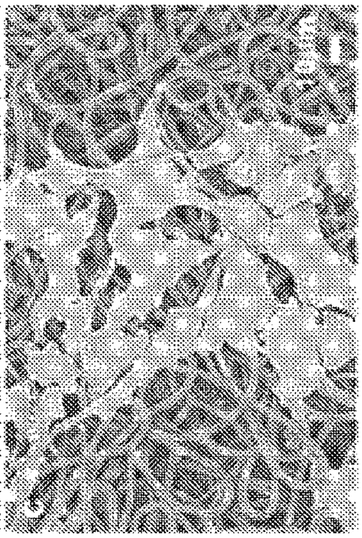
Figure 2D:
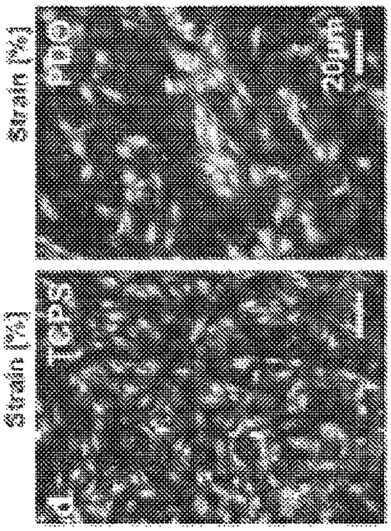
Figure 2E:
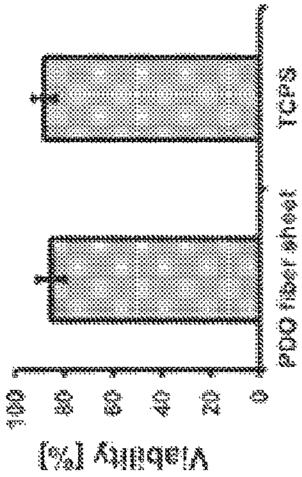

Scaffolds were constructed with PDO since it is strong, degrades within 6 months, and has established biocompatibility. PDO exhibits similar mechanical properties to polycaprolactone (PCL, which is commonly electrospun) but degrades in half the time or less. Electrospun PDO revealed well-defined microfibers with 1.5 μm average diameter. Uniaxial tensile testing demonstrates that PDO fibrous scaffolds are suturable (FIG. 2B). Fibrous PDO scaffolds demonstrate a suture retention strength of 142 N $mm^{-2}$ (FIG. 2B). Tensile strain to failure shows a linear region with a modulus of 29.7 MPa up to 10% strain and failure at 9.6 MPa stress and over 200% strain (FIG. 2B). Cyclic testing shows that PDO exhibits plastic deformation at 50% strain during the first cycle but remains constant afterwards (FIG. 2B). In vitro culture of human umbilical vein endothelial cells (HUVECs) nn electrospun PDO fibers demonstrated good attachment as indicated by the sprawled morphology (FIG. 2C). The Live/Dead assay showed viability on electrospun PDO (85%) similar to that on TCPS (88%) (FIG. 2D).

Figure 3C:
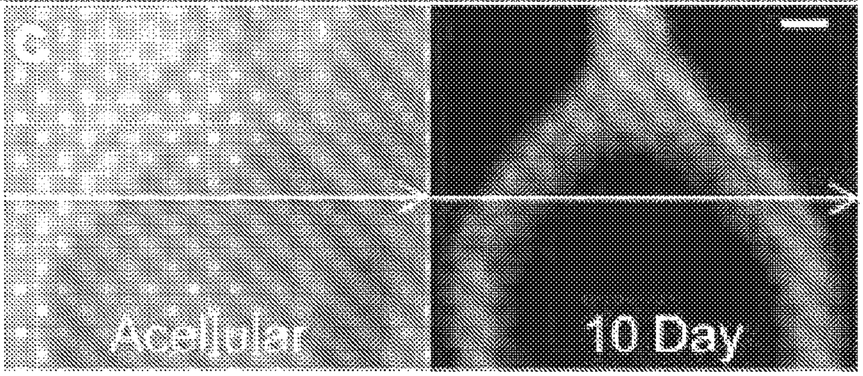
Figure 3D:
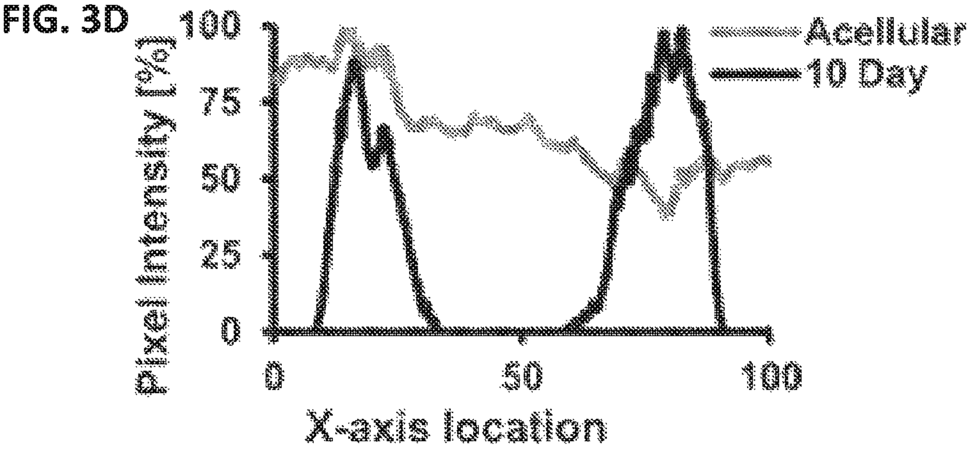
Figure 4:
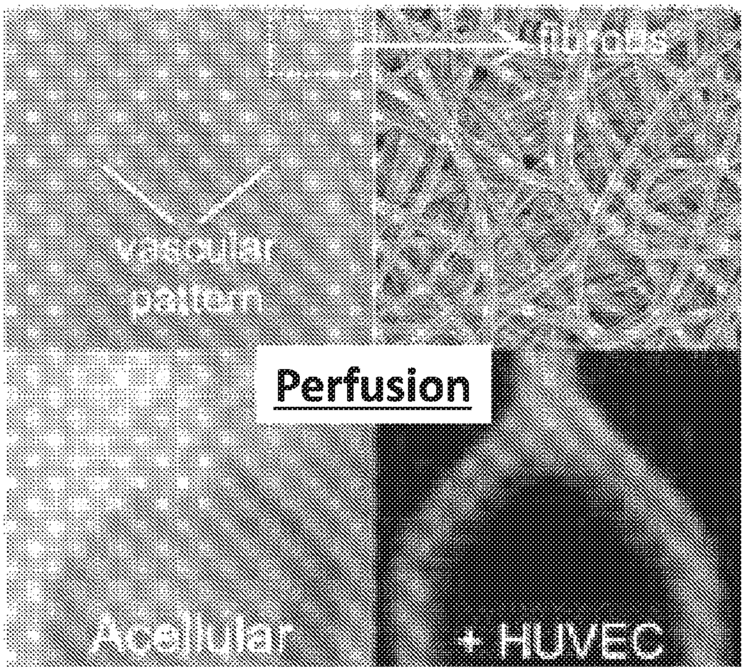
FIG. 4 a series of images illustrating fibrous microvascular scaffolds made by hybrid electrospinning-additive manufacturing.
Figure 5A:
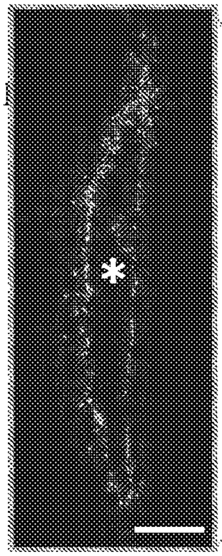
FIGS. 5A-5B provide DAPI stained images of human umbilical cord vascular endothelial cells (HUVEC) in microvascular scaffolds for 1 day.
Figure 5B:
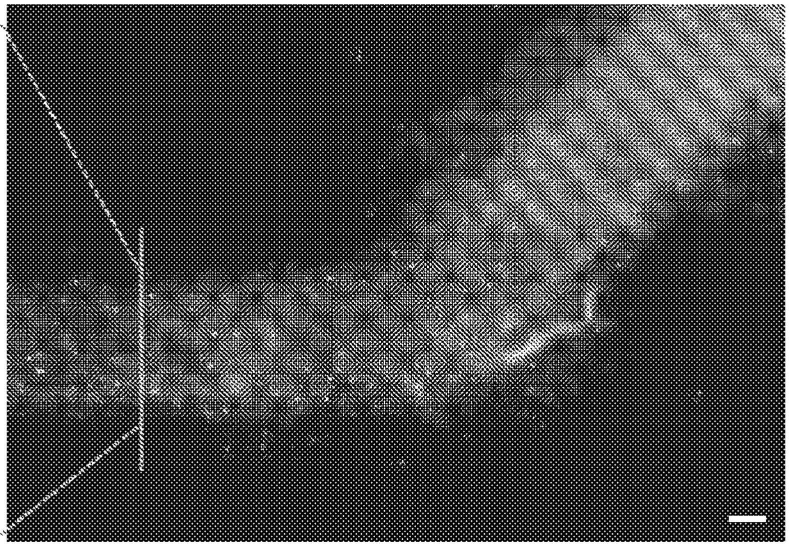

The fibrous nature of the microvascular scaffold greatly enhances diffusion. In fact it is leaky, therefore these scaffolds were seeded through a filter-like process, whereby fluid from the injected cell suspension passes through the fibers while trapping the cells against the channel walls. This seeding method takes advantage of the poor cell infiltration into electrospun constructs, identified as a problem in literature. HUVECs attached and proliferated on the PDO fibers and formed a near-confluent layer after 10 days. The cells formed adheren junctions along the channel as demonstrated by VE-cadherin and CD31 staining (top-view) (FIG. 3A). The position of HUVECs in the scaffold was further revealed by DAPI and vWF staining of the channel cross-sections (FIG. 3B). Maturation of the HUVECs and confluence of EC layer were estimated by perfusing fluorescein isothioeyanate (FITC)-labeled dextran solution in the lumen (FIG. 3C). The cultured microvessels show a drastic reduction in leakiness compared to the unseeded scaffold. However, some leaking still occurred, which might be due to either incomplete coverage of the lumen or insufficient tight junction formation from seeded HUVECs. It is believe that increased culture time and co-culturing of mural cells such as pericytes will yield water-tight vessels. FIG. 4 further illustrates fibrous microvascular scaffolds made by hybrid electrospinning-additive manufacturing process disclosed herein. FIGS. 5A-5B demonstrate DAPI stained images of (HUVEC) in microvascular scaffolds for 1 day. This in vitro culture demonstrates formation of endothelial monolayers. FIG. 6 illustrates combining electrospinning with 3D printing on the same platform. The panel on the left provides a computer model. The panel on the tight includes a series of digital images of a modified Lulzbot for electrospinning ((1) Motorized electrospinning needle gantry; (2) Solvent dropper (for removal of electrospun fiber); (3) Spring switch for activating/deactivating collector voltage; and (4) Modified build platform/electrospinning collector plate.

The fabrication technique described here lays the foundation for introducing microvascular structure into electrospun scaffolds. The thin (<100 μm) fibrous channel walls will improve perfusion of parenchymal cells. This overcomes several significant challenges of engineered microvasculatures including low perfusion capacity, inability to suture, poor strength associated with hydrogel approach, and nonciegradability for PDMS based approaches.

Example 3

This example demonstrates a method of fabricating a PGS microvascular scaffold and uses of such scaffold.

Figure 7A:
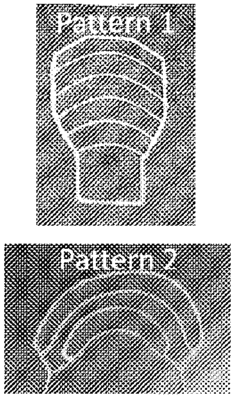
FIGS. 7A-7C illustrate an exemplary fabrication process part 1: pattern electrospun fibers with template.
Figure 7B:
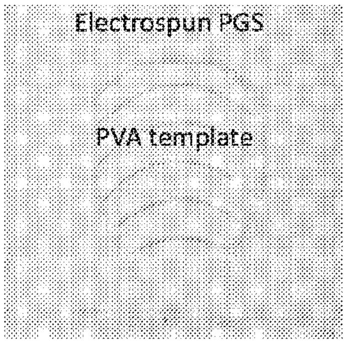
Figure 7C:
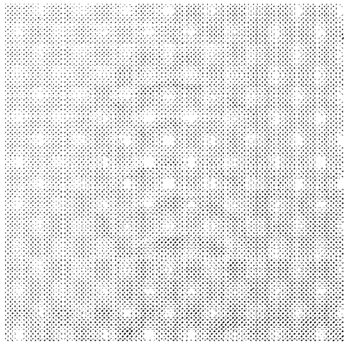

A PGS microvascular scaffold was fabricated by the following three step fabrication process: (1) pattern electrospun fibers with template (see FIGS. 7A-7C); (2) crosslink and purify PGS constructs (see FIGS. 8A-8B); and (3) embed vasculature in a porous matrix (see FIGS. 9A-9B). As illustrated in FIGS. 7A-7C, a 3D print PVA template (FIG. 7A) was placed on a sheet of electrospun PGS (FIG. 7B) and a second layer of PGS was then electrospun on top of the PVA template. Then, the resulting construct was crosslinked by assembling inlet/outlet PGS tubes within the PGS-template construct and placing the entire assembly into a TEFLON mold (FIG. 8A) and applying heat at 120° C. for 48 hours. Tubular inlet/outlet ports were fabricated as previously described in PCT/US2013/077226 which is hereby incorporated by reference in its entirety. TEFLON molds were used to prevent warping/curling of the PVA templates during crosslinking. The molds were also used to apply moderate pressure to select locations to facilitate better adhesion between layers of electrospun PGS layers. In the present example, the inlet and outlet PGS tubes were placed on the same side of the construct as for some tissues it is beneficial to have the arterial and venous anastomosis sites on the same side. Further, PGS inlet/outlet tubes fabricated by rotational electrospinning were stronger and suitable for anastomosis. Other configurations are contemplated such as the tubes being placed on opposite sides. This was followed, by purifying the PGS by use of ethanol/water washes. The resulting PGS microvascular scaffold was then embedded into a porous matrix such as a cast collagen/glycosaminoglycans(GAG) matrix (FIG. 9A) or PGS prepolymer was electrosprayed to the top and bottom of the microvascular scaffold, salt-leached PCS sheets were adhered to PGS sheets to PGS prepolymer and secured by heat crosslinking (FIG. 913). The resulting porous structure is shown in the SEM image provided in FIG. 9B. Thus, the disclosed method resulted in highly porous matrices which create 3-dimensional scaffolds for cell ingrowth from the host or cell seeding for tissue engineered organ approaches.

FIGS. 1A-1C provide images of use of a fabricated PGS scaffold in a rat arterio-venous (AV) shunt model. Implantation into the rat carotid artery/jugular vein was performed to demonstrate scale of construct in addition to feasibility of anastomosis with host vasculature and patency of the fabricated microvessels in vivo.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A fibrous construct formed by:
electrospinning a first layer of fibrous material;
printing a micropatterned sacrificial template comprising a user-defined pattern for producing at least one channel or microstructure;
placing the micropatterned sacrificial template onto the first layer of fibrous material;
electrospinning a second layer of fibrous material onto the micropatterned sacrificial template thereby encapsulating the template and generating a construct comprising the first layer and the second layer of electrospun fibrous material and the micropatterned sacrificial template;
removing the sacrificial template; and
generating the fibrous construct patterned with the at least one channel or microstructure produced by removing the sacrificial template, wherein the at least one channels or microstructures extends through the fibrous construct.

2. The fibrous construct of claim 1, further comprising a pharmaceutical agent.

3. A scaffold made from the fibrous construct of claim 1.

4. The scaffold of claim 3, further comprising cells.

5. A vascular structure comprising the scaffold of claim 3, wherein the scaffold comprises an inner and an outer luminal surface, and wherein the inner luminal surface of the scaffold has a thromboresistant agent coating, thereby providing a patent blood flow upon implantation.

6. The fibrous construct of claim 1, wherein the first layer of fibrous material is poly(glycerol sebacate) (PGS), polydioxanone (PDO), PGS prepolymer, poly(caprolactone) (PCL), polyhydroxybutyrate (PHB), poly(styrene-block-isobutylene-block-styrene) (SIBS), gelatin, or a combination thereof.

7. The fibrous construct of claim 1, wherein the second layer of fibrous material is poly(glycerol sebacate) (PGS), polydioxanone (PDO), PGS prepolymer, poly(caprolactone) (PCL), polyhydroxybutyrate (PHB), poly(styrene-block-isobutylene-block-styrene) (SIBS), gelatin, or a combination thereof.

8. The fibrous construct of claim 1, wherein the patterned at least one channel& or microstructure patterned in the fibrous construct is configured to allow infiltration of cells into the fibrous construct.

9. The fibrous construct of claim 1, wherein the at least one channel or microstructure patterned in the fibrous construct comprises an interconnected channel pattern.

10. The fibrous construct of claim 1, wherein a diameter of the at least one patterned channel or microstructure is between 0.01 mm to 1 mm, and a matrix porosity of the fibrous construct is between 1 μm to 500 μm.

11. A method for fabricating a fibrous construct, comprising:
electrospinning a first layer of fibrous material;
printing a micropatterned sacrificial template comprising a user-defined pattern for producing at least one channel or microstructure;
placing the micropatterned sacrificial template onto the first layer of fibrous material;
electrospinning a second layer of fibrous material onto the micropatterned sacrificial template thereby encapsulating the template and generating a construct comprising the first layer and the second layer of electrospun material and the micropatterned sacrificial template;
removing the sacrificial template; and
generating the fibrous construct patterned with the at least one channel& or microstructure& produced by removing the sacrificial template, wherein the at least one channel or microstructure extends through the fibrous construct.

12. The method of claim 1, wherein the fibrous construct also contains cells covering a luminal surface of the at least one channel& or microstructure.

13. The method of claim 12, wherein the cells comprise one or more of myocytes, epithelial cells, hepatocytes, islet cells, podocytes, neuronal cells, endothelial cells, and other cells associated with vital organs including heart, lung, liver, pancreas, kidney, and nerve.

14. The method of claim 11, wherein the first layer of fibrous material is poly(glycerol sebacate) (PGS), polydioxanone (PDO), PGS prepolymer, poly(caprolactone) (PCL), polyethylene terephthalate (PET), polyhydroxybuytrate (PHB), poly(lactic-co-glycolic acid) (PLGA), poly(styrene-block-isobutylene-block-styrene) (SIBS), collagen, gelatin, or a combination thereof.

15. The method of claim 1, wherein the second layer is poly(glycerol sebacate) (PGS), PGS prepolymer, polydioxanone (PDO), poly(caprolactone) (PCL), polyethylene terephthalate (PET), polyhydroxybutyrate (PHB), poly(lactic-co-glycolic acid) (PLGA), poly(styrene-block-isobutylene-block-styrene) (SIBS), collagen, gelatin, or a combination thereof.

16. The method of claim 11, wherein the first layer of fibrous material and the second layer of fibrous material are the same fibrous material.

17. The method of claim 8, wherein the fibrous material is poly(glycerol sebacate) (PGS), PGS prepolymer, or polydioxanone (PDO).

18. The method of claim 11, wherein the first layer of fibrous material and the second layer of fibrous material are different fibrous material.

19. The method of claim 11, wherein electrospinning the first layer of fibrous material comprises electrospinning onto an aluminum collector.

20. The method of claim 11, wherein the micropatterned sacrificial template is formed of a water-soluble substance.

21. The method of claim 11, wherein printing a micropatterned sacrificial template is by additive manufacturing.

22. The method of claim 11, wherein removing the sacrificial template comprises dissolving the sacrificial template in water.

* * * * *